(12) United States Patent
Foser et al.

(10) Patent No.: US 7,491,059 B2
(45) Date of Patent: Feb. 17, 2009

(54) DENTAL CONNECTING APPARATUS

(75) Inventors: Hans-Peter Foser, Balzers (LI); Eugen Gassner, Triesen (LI)

(73) Assignee: Ivoclar Vivadent AG, Schaan (LI)

( * ) Notice: Subject to any disclaimer, the term of this patent is extended or adjusted under 35 U.S.C. 154(b) by 397 days.

(21) Appl. No.: 10/866,374

(22) Filed: Jun. 10, 2004

(65) Prior Publication Data
US 2005/0037321 A1    Feb. 17, 2005

(30) Foreign Application Priority Data
Aug. 14, 2003   (DE) .............................. P 103 37 462

(51) Int. Cl.
*A61C 13/12*   (2006.01)
(52) U.S. Cl. ...................................................... 433/181
(58) Field of Classification Search ......... 433/181–183, 433/190, 194, 195
See application file for complete search history.

(56) References Cited

U.S. PATENT DOCUMENTS

| | | | | |
|---|---|---|---|---|
| 1,297,561 A | * | 3/1919 | Guntner ....................... | 433/181 |
| 1,698,259 A | * | 1/1929 | Craig .......................... | 433/181 |
| 1,753,644 A | * | 4/1930 | Burden ........................ | 433/181 |
| 4,431,420 A | * | 2/1984 | Adair .......................... | 106/35 |
| 4,608,020 A | * | 8/1986 | Laszlo ......................... | 433/213 |
| 4,661,068 A | * | 4/1987 | Harrison et al. ............. | 433/181 |
| 4,711,631 A | * | 12/1987 | Thomsen .................... | 433/181 |
| 4,744,757 A | * | 5/1988 | Adair et al. ................. | 433/180 |
| 5,092,772 A | * | 3/1992 | Seaton ........................ | 433/182 |
| 5,927,984 A | * | 7/1999 | Lin ............................. | 433/218 |
| 6,394,810 B1 | * | 5/2002 | Choi .......................... | 433/180 |

FOREIGN PATENT DOCUMENTS

| | | |
|---|---|---|
| DE | 35 40 049 A1 | 5/1987 |
| EP | 0 887 049 A1 | 12/1998 |
| GB | 2 147 505 A | 5/1985 |

* cited by examiner

*Primary Examiner*—Melba Bumgarner
(74) *Attorney, Agent, or Firm*—John C. Thompson; Alan S. Kormay

(57) ABSTRACT

A connecting apparatus for connecting an item, especially a dental prosthetic device, with an anchor tooth or a crown in the mouth of a dental patient. The connecting apparatus includes a first interconnecting element (14, 16) for connecting the dental prosthetic device with the selected one of the anchor tooth and the crown in the mouth of a dental patient and a second interconnecting element (26, 28). The first interconnecting element (14, 16) includes a positive coupling piece (22, 24) formed of ceramic. The second connecting element is a negative coupling piece (26, 28) comprised of glass fiber reinforced synthetic material, at least in a wear region thereof which lies against the first interconnecting element 14. The positive and negative coupling pieces are securable to one another in a mated shape closure manner.

6 Claims, 4 Drawing Sheets

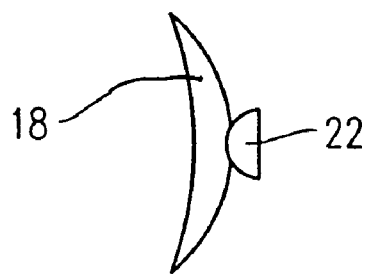
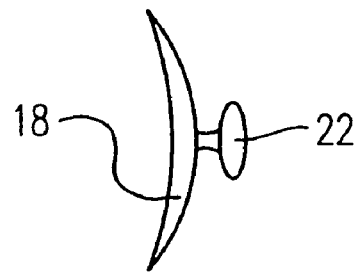
Fig. 4　　　　　　　　Fig. 5
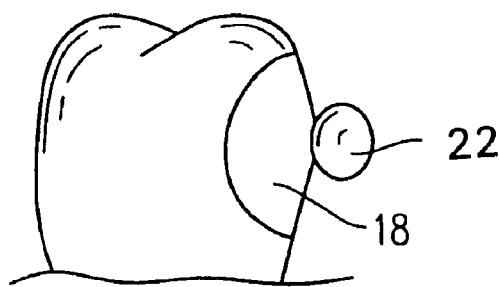
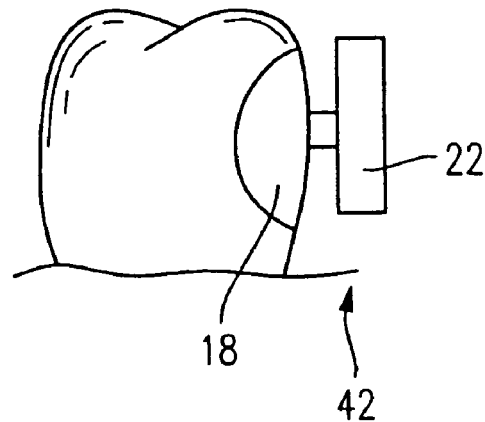
Fig. 6　　　　　　　　Fig. 7

DENTAL CONNECTING APPARATUS

CROSS-REFERENCE TO RELATED APPLICATIONS

This application claims foreign priority benefits under 35 U.S.C. §119 from German patent application Ser. No. 103 37 462.0 filed Aug. 14, 2003.

TECHNICAL FIELD

The present invention relates to a dental connecting apparatus for dental prosthetic devices.

BACKGROUND OF THE INVENTION

As a basic principle, dental prosthetic devices, especially partial and hybrid dental prosthetic devices, must be secured via suitable interconnecting elements on anchor teeth and/or crowns, hereinafter referred to as anchor teeth. This is typically effected via metallic construction elements, mainly in the form of connecting pieces between natural teeth structure and dental prosthetic devices, whereby principally high value stainless steel coatings, titanium, nonferrous metals are deployed for such purposes, with these materials forming two compatibly configured interconnecting elements namely, a positive coupling piece and a negative coupling piece.

Such metallic configurations bring with them the disadvantage that the biocompatibility thereof can be improved.

EP-A1-0 887 049 discloses a dental connecting apparatus which, in lieu of a metallic base construction, realizes the connection via ceramic material which is applied either as the exclusive material or as a coating. Coatings have, on the other hand, the disadvantages that the typically different heat expansion coefficients between metals and a ceramic require very careful application of the ceramic coating and, in view of the substantially brittle characteristic of the ceramic, the coating must be markedly thick if it is to have good durability.

The above-noted publication describes, in any event, a solution whereby conventional positive coupling pieces and negative coupling pieces comprised of ceramic filling material are presented as the improved technical solution.

Moreover, the above-noted publication discloses as well the provision of a synthetic material or plastic coating on the ceramic material in order to improve the slide capability of the positive coupling pieces and negative coupling pieces. This solution has the disadvantage that the synthetic material coating, which has only a negligible secure holding characteristic, precisely in connection with its deployment on the positive coupling piece leads to a weakening of the material thickness available for assuring the tenaciousness of the piece, so that the positive coupling piece is in danger of breaking. It is, therefore, not surprising that this solution has not found wide usage.

It has also already been suggested, in lieu of the afore-described solutions, to improve the aesthetic appearance of the dental prosthetic devices with pure mixture materials for metallic connecting pieces between natural teeth structure and dental prosthetic devices, whereby the functional portions that is, the areas of the positive coupling pieces and negative coupling pieces which are disposed in opposition to one another are comprised of substantial amounts of metallic material. In this manner, the bio-compatibility is somewhat improved; a completely sealed configuration of the coupling securement, which would seal off the metallic outer surfaces, has not yet, however, been achieved in connection with this solution.

SUMMARY OF THE INVENTION

The present invention provides a solution to the challenge of providing a dental connecting apparatus which offers an improved bio-compatibility while, at the same time, offering long-term stability and facilitating easy handling thereof.

Via the inventive combination of ceramic for the one interconnecting element, on the one hand, and glass fiber reinforced synthetic material for the other interconnecting element, on the other hand, with each interconnecting element preferably being configured as a solid or molar mass, there is unexpectedly achieved a particularly good securement, which is also stable over the long term. Surprisingly, the application or disposition of short length glass fibers and, as well, the application or disposition of comparatively long length glass fibers, does not disturb the slide capability of the connecting piece between natural teeth structure and dental prosthetic devices.

In accordance with the present invention, it is important to ensure an exact accommodation of the ceramic and glass fiber reinforced synthetic material to one another, in view of their different heat expansion coefficients, and to ensure a zero-free play disposition at mouth temperature.

In accordance with the present invention, it is particularly advantageous if the negative coupling pieces, if they are fully or substantially comprised of glass fiber reinforced synthetic material, are secured and surrounded by a region of the dental prosthetic device which itself is formed to simulate a tooth appearance so that the already increased securement characteristic of the glass fiber reinforced synthetic material is still further reinforced by the mounted disposition of the interconnecting elements.

In accordance with the present invention, it is also particularly advantageous that an interconnecting element of this type is configured as a slide wear portion and is exchangeable.

This inventive solution permits the production, without supplemental measures, of the glass fiber reinforced synthetic material in the desired anchor tooth color and there is no requirement of an expensive covering removal effort in order to make ready a natural color anchor tooth.

The connection can be realized, without supplemental measures, by means of dental prosthetic device synthetic material, which further supports the mated shape closure between negative coupling pieces and positive coupling pieces. In accordance with the present invention, it is also advantageous that no corrosion can occur and a minimally invasive solution is made possible. The positive coupling pieces, which are themselves comprised of zirconium oxide, aluminum oxide, or lithium disilicate-glass ceramic, can be secured via their securement sockets on an anchor tooth or, as the occasion arises, on a crown, whereby it is to be understood that the location of the anchor tooth or the post tooth or, respectively, the crown, can be selected as desired and the securement socket can be configured in a flush orientation to this anchor region.

The positive coupling pieces can be configured in a desired manner in a ball shape, a spherical shape, or a partially spherical shape, whereby it is to be understood that the negative coupling pieces are comprised of a correspondingly compatibly configured configuration, which permits a secure mechanical anchoring and interconnection. Preferably, the withdrawal direction is precisely along, or substantially precisely along, the occlusal direction, whereby a withdrawal, on the one hand, and a reliably secure interconnection, on the other hand, are facilitated by a slightly conical configuration of the mutually opposed outer surfaces.

In an advantageous embodiment of the present invention, it is also possible to produce the inventive dental connecting apparatus by use of an anchor tooth model. In accordance with this embodiment, a place holder or the additional or second interconnecting element, which is already prepared, is inserted onto the first interconnecting element. The free play space between these interconnecting elements and the gums is filled with a filling mass. By means of an impression mass, an impression of the anchor tooth or, respectively, of the crown, and the free play area is taken and a tooth model based upon the tooth situation in the mouth of the patient is derived therefrom.

The just noted embodiment provides a particularly good stability in that a high strength ceramic can be deployed. In one embodiment of the present invention, it is provided that the negative coupling piece can be released from the positive coupling piece without the need for a tool, while, in another embodiment, the negative coupling piece and positive coupling piece can be separated from one another via a tool.

In one modification of an embodiment of the present invention, it is provided that suitable desired forms of inlays, onlays, or overlays are realized via the inventive solution as well as other types of partial or full crowns or the application of an exterior-to-the tooth crown attachment on a bridge.

Further advantages, details, and features of the present invention can be found in the hereinafter-following description of an embodiment of the present invention with reference to the figures of the drawings.

BRIEF DESCRIPTION OF THE FIGURES

FIG. 4 is a side elevational view of a further modification of the inventive positive coupling piece;

FIG. 5 is a side elevational view of another modification of the inventive positive coupling piece;

FIG. 6 is a side elevational view of an additional further modification of the inventive positive coupling piece mounted on an anchor tooth;

FIG. 7 is a side elevational view of yet another further modification of the inventive positive coupling piece, this coupling piece also being mounted on an anchor tooth;

DETAILED DESCRIPTION OF PREFERRED EMBODIMENT

Figure 1:
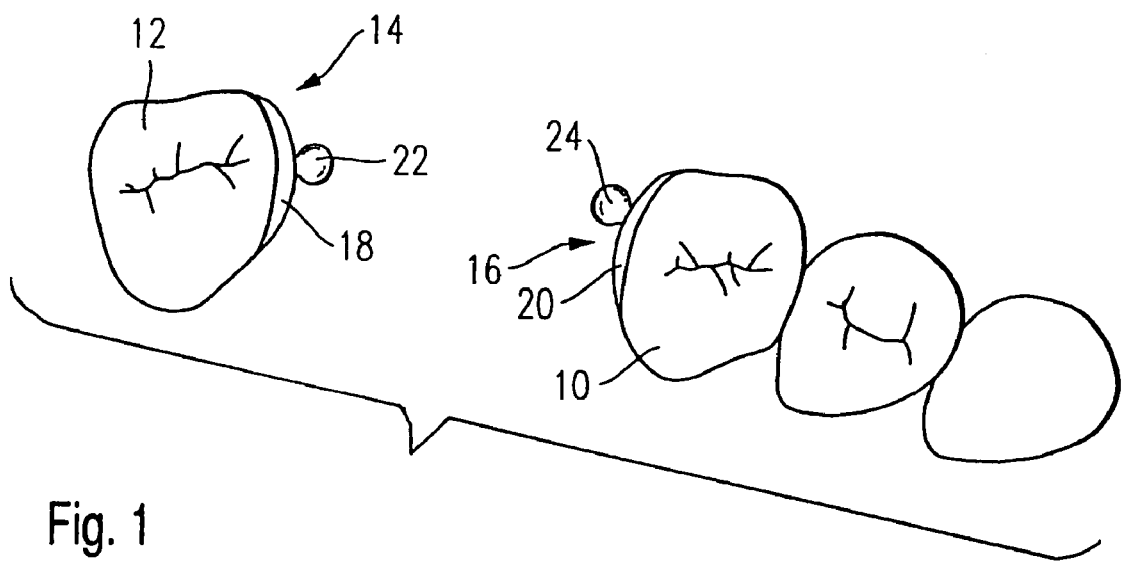
FIG. 1 is a top plan view of a mouth situation of a dental patient and showing a representation of two interconnecting elements comprising a portion of one embodiment of the inventive dental connecting apparatus.

FIG. 1 illustrates one manner in which the dental connecting apparatus of the present invention can be realized. Interconnecting elements, indicated generally at 14 and 16, have positive coupling pieces 22, 24. The elements are each mounted on a respective one of an anchor tooth 10 or an anchor tooth 12. The interconnecting elements 14 and 16 have specially configured securement sockets 18 and 20, respectively, which are formed outwardly of the interconnecting elements to have a harmonious appearance therewith and, in fact, are joined to the distal or, respectively, the medial (mesial), side surfaces of the respective anchor teeth and are securely fastened thereto by means of a cement medium.

In the embodiment of FIG. 1, the positive coupling pieces 22, 24 of the interconnecting elements 14, 16, respectively, are each substantially spherically shaped, whereby the positive coupling pieces offer a receipt surface around a wrap- or loop-around angle of approximately 270° and, otherwise, are integrally formed with the respective securement socket 18 or 20. The securement socket (18, 20) may be at least partially formed of a plastically deformable material which can be accommodated to the outer contour of the anchor tooth. This solution provides, on the one hand, a high degree of securement and, on the other hand, a secure mated shape connection. In this embodiment each interconnecting element, including the positive coupling piece, is comprised of lithium disilicate-glass ceramic and is secured in a conventional manner via a cement medium or adhesive to the respective anchor tooth 10, 12.

Figure 2:
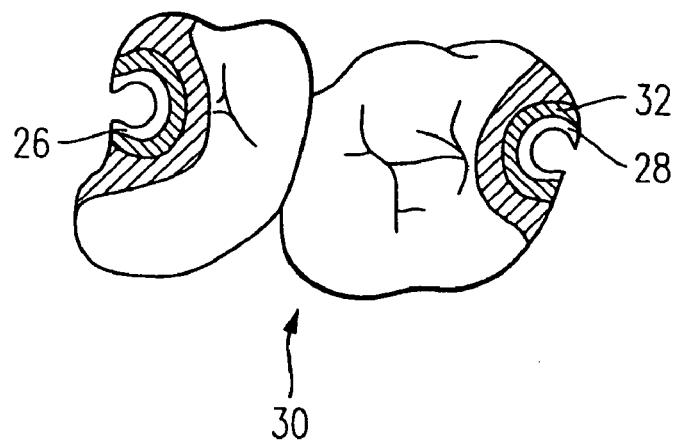
FIG. 2 is a top plan view, in partial section, of the second one of the interconnecting elements shown in FIG. 1 showing a portion of a partial dental prosthetic device.
Figure 13:
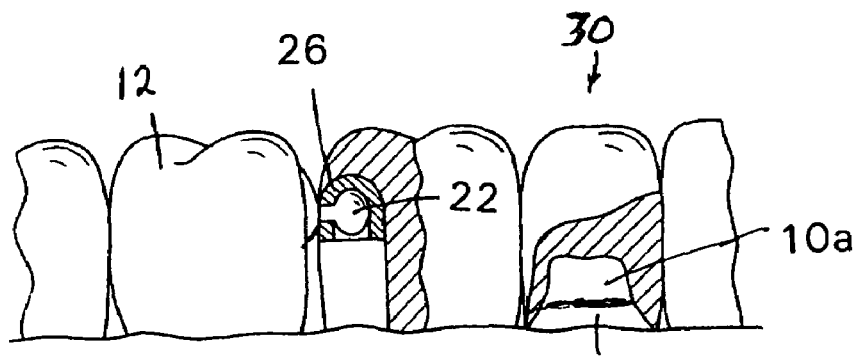
FIG. 13 shows the bridge of FIG. 12 mounted on the two anchor teeth of FIG. 8, the bridge having been provided with a positive coupling piece.

FIG. 2 shows the manner in which the negative coupling pieces 26 or, respectively, 28, each of which serves as the second inventive interconnecting element, can be secured to a partial dental prosthetic device, indicated generally at 30. The negative coupling pieces 26, 28 are each respectively mounted, via dental prosthetic device synthetic material or a cement medium or adhesive 32, on the partial dental prosthetic device 30, whereby, in the configuration shown in FIG. 2, the thickness of the dental prosthetic device synthetic material is shown in an exaggerated manner relative to the depiction of the thickness of the negative coupling piece. The negative coupling pieces 26, 28 are comprised of glass fiber reinforced synthetic material and comprise an interior shape which exactly corresponds to the respective outer shape of the positive coupling pieces 22 or, respectively, 24. The negative coupling pieces are open downwardly and closed on their upper side, as can best be seen from FIG. 13.

Figure 3:
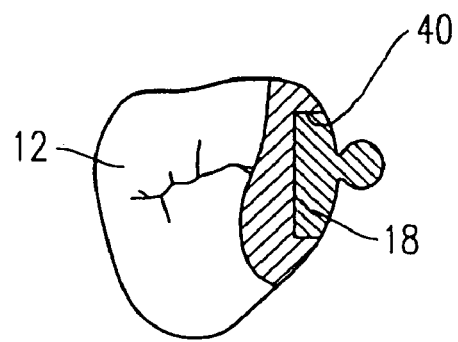
FIG. 3 is a top plan view, in partial section, of a modification of one embodiment of the inventive first interconnecting element namely, the positive coupling piece.
Figure 8:
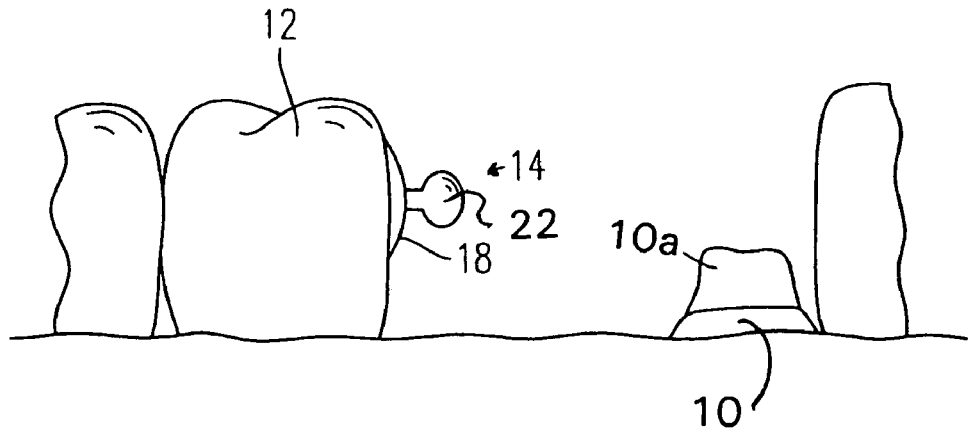
FIG. 8 is a side elevational view showing two anchor teeth, one of which is provided with an embodiment of the dental connecting apparatus in the form of a positive coupling piece.

As can be seen in FIG. 3, the securement socket 18 can be configured in a different configuration. Similarly, although not illustrated, the securement socket 20 may also be configured in a different configuration. In FIG. 3 the anchor tooth 12 is provided with a pot-shaped recess, indicated generally at 40, which recess is preformed on the anchor tooth in a manner which is minimally invasive from the point of view of stock reduction of the anchor tooth, whereby the recess is available for subsequent receipt therein of the securement socket 18.

The respective embodiments shown in FIGS. 4 and 5 correspond substantially to the embodiments of the securement socket shown in FIG. 1, whereby the projecting portion of the positive coupling piece 22 has a different configuration in each respective embodiment.

As seen in FIG. 4, a half-spherical configuration is provided while the embodiment shown in FIG. 5 has been provided with a more lens-shaped configuration. In this connection, the possibility exists to accommodate the desired shape to a wide range of requirements and desired configurations, whereby it should constantly be ensured that a good configuration compatibility and a secure mechanical anchoring between the positive coupling pieces 22 and the negative coupling pieces 26 are provided.

Further configuration possibilities of the positive coupling pieces are shown in FIGS. 6 and 7. FIG. 6 shows a solution for the securement socket 18, which is more pronouncedly invasive and can be deployed in connection with problematic securement situations. In contrast, FIG. 7 shows a configuration of the positive coupling piece 22 which is substantially cylindrically rod-shaped and which offers, as well, a good support against tipping demands. It is to be understood that the connection region, indicated generally at 42, between the projecting portion of the positive coupling piece 22 and the securement socket 18 can be accommodated to requirements over a wide range, but, however, should be configured in any event to foreclose the risk of breakage. It should be apparent that the coupling piece may have many differing configurations. Thus, the positive coupling piece 22 is substantially rod shaved, has a central longitudinal axis generally extending in the occlusal direction, and has a selected one of a round, a partially round, and an oval cross-section, the cross-section tapering slightly conically inwardly in the occlusal direction.

In the embodiments of FIGS. 1-7 the withdrawal of the partial dental prosthetic device 30 is possible via the deployment of a suitable tool. A withdrawal is also possible by means of a corresponding hand force application, the configuration accommodation being chosen to permit such withdrawal.

It is to be understood that the material choice of comparatively elastic glass fiber reinforced synthetic material, on the one hand, and of ceramic material, on the other hand, permits a good securement. It is also possible to produce the positive coupling pieces with somewhat exaggerated dimensions, which makes possible, on the one hand, a substantially long-term connection and, on the other hand, makes possible the withdrawal of the positive coupling pieces and the negative coupling pieces from one another via exploitation of the elastic property of the glass fiber reinforced synthetic material.

FIGS. 8 to 11 and 13 show anchor teeth, one of which is provided with an interconnecting element 14, and the other with a prepared tooth stump 10a. These figures also show the inventive method for producing a partial dental prosthetic device 30. While the method illustrated shows a partial dental prosthetic device 30 which is to be secured to an interconnecting element 14 and a prepared tooth stump 10a of an anchor tooth 10, the method may also be used to produce a partial dental prosthetic device 30 of the type illustrated in FIG. 2. In accordance with a preferred method, interconnecting elements 14 and/or 16 are initially produced. Each element is mounted on an anchor tooth. In the illustrated method, only element 14 is shown being mounted on anchor tooth 12, the element including a securement socket 18 and a positive coupling piece 22.

Figure 9:
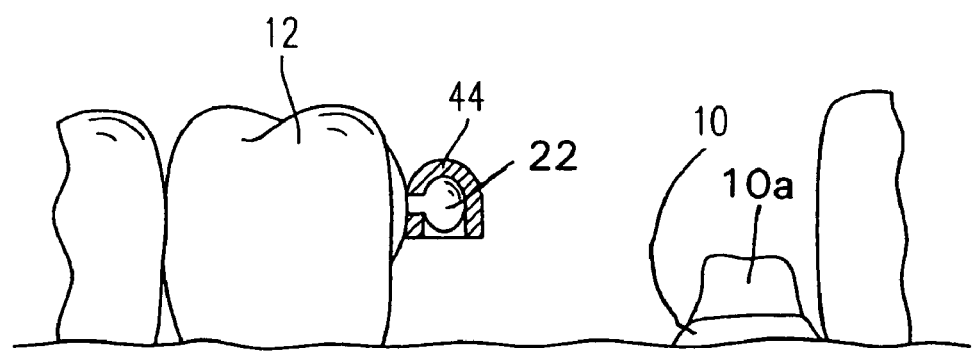
FIG. 9 is similar to FIG. 8, but showing a place holder inserted on the positive coupling piece.

As shown in FIG. 9, a place holder 44 is placed onto the positive coupling piece 22 of the first interconnecting element 14. Alternatively, a negative coupling piece 26 may be used.

Figure 10:
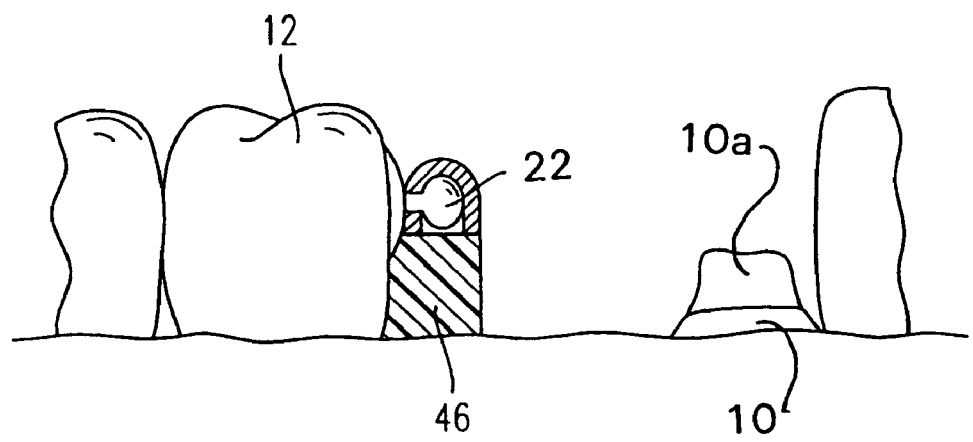
FIG. 10 shows the play space below the place holder shown in FIG. 9 filled with a filling mass.
Figure 11:
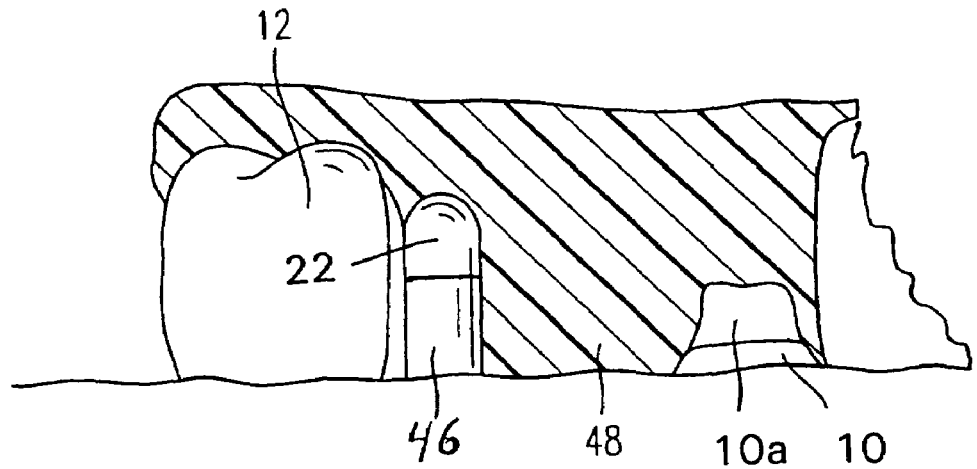
FIG. 11 shows an impression mass inserted.
Figure 12:
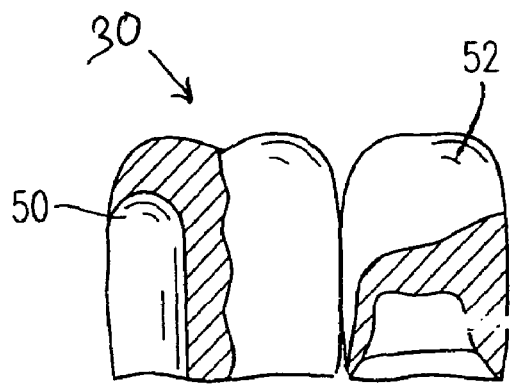
FIG. 12 shows the bridge made from the impression mass of FIG. 11.

As shown in FIG. 10, a filling mass 46 is placed in the free play space below the interconnecting element 14 and the place holder 44 (or negative coupling piece 26) and above the gum (no reference numeral) of the patient. As shown in FIG. 11, an impression mass 48 is placed in the prepared area to take an impression of the respective natural or artificial tooth structure and the free play area. After the impression mass 40 is removed from the patient's mouth, the place holder 44 (or negative coupling piece 26) and the filling mass are also removed from the patient's mouth. From the impression, a bridge or a tooth model 30 is created. Various techniques, well known to those skilled in the art may be used. One such method includes the steps of making a hard stone model from the impression. Using the hard stone model, a dental technician will create a wax model of the dental restoration. Now the technician will place investment material about the wax model. After setting, the investment material and wax model are placed in an oven for a length of time sufficient for all wax to vaporize, forming a mold cavity where the wax has been lost, After this step has been completed, a suitable dental material, after it has been heated to a softened condition, is pressed into the mold cavity to form the desired dental restoration. After the mold has been filled with the dental material, the investment mold is removed from the furnace and is allowed to cool to room temperature. The dental restoration 30 is then divested from the investment material. The dental restoration may now be finished. The finishing may include either staining or layering, and these techniques are well known to those skilled in the art. As can be seen, the dental restoration 30, formed by the above process has a cavity 50, representing the place bolder 44 and the filling mass 46. As shown in FIG. 11, the bridge may have two teeth, one of which is indicated at 52, the tooth 52 having a cavity for the reception of a prepared tooth stump 10a.

A second interconnecting element 26 is now integrated into the model 30. This can be done by disposing the second interconnecting element (or negative coupling piece) 26 on the first interconnecting element (or positive coupling piece) 22 in the mouth of the dental patient. A curable material which can be hardened by light irradiation thereof is applied to the exterior surface of element 26. The dental prosthesis 30 is now placed in the mouth of the dental patient, and the curable material is hardened by light irradiation thereof to connect second interconnecting element 26 and the dental prosthesis.

The positive coupling piece 22 and the negative coupling piece 26 are formed of materials having substantially the same heat expansion coefficient. The first interconnecting element is formed of ceramic, and the negative coupling piece is at least partially formed of glass fiber reinforced synthetic material.

While preferred forms of this invention has been described above and shown in the accompanying drawings, it should be understood that applicant does not intend to be limited to the particular details described above and illustrated in the accompanying drawings, but intends to be limited only to the scope of the invention as defined by the following claims. In this regard, the term "means for" as used in the claims is intended to include not only the designs illustrated in the drawings of this application and the equivalent designs discussed in the text, but it is also intended to cover other equivalents now known to those skilled in the art, or those equivalents which may become known to those skilled in the art in the future. Furthermore, while the interconnecting elements 14, 16 are shown mounted on anchor teeth 12, 10, respectively, they may be mounted on synthetic anchor teeth of the dental prosthetic device 30, in which case the negative coupling pieces 26, 28 would be mounted on the anchor teeth.

What is claimed is:

1. A method for producing a dental restoration adapted to connect to a natural or artificial tooth structure, the dental restoration having at least one connecting piece which secures to at least one other connecting piece on the natural or artificial tooth structure, the connecting pieces being releasably interconnectable with one another, the method comprising:

mounting a first interconnecting element (14, 16) on an anchor tooth of a dental patient, the first interconnecting element being secured on an outer side of the anchor tooth (12) and on an outer distal or medial side thereof;

inserting a selected one of a place holder (44) and a second interconnecting element (26, 28) onto the first interconnecting element (14, 16);

filling a free play space between the respective selected one of the place holder and the second interconnecting element, on the one hand, and gum of the dental patient, on the other hand, with a filling mass (46);

taking an impression of the respective natural or artificial tooth structure (12) and the mass filled free play space by means of an impression mass (48);

making a hard stone model from the impression;

creating a wax model of the dental restoration using the hard stone model, the wax model having a cavity which corresponds to the filing mass and the selected one of the place holder (44) and the second interconnecting element (26, 28);

embedding the wax model in mold material;

vaporizing the wax to leave a mold cavity in the mold material; and heating ceramic material to a softened state;

pressing the softened ceramic material into the mold cavity to produce a partial dental restoration;

securing a positive coupling piece in the cavity which corresponds to the selected one of the place holder (44) and the second interconnecting element (26, 28) to produce a dental restoration.

2. A method according to claim 1 and further comprising removing the selected one of place holder and the second interconnecting element after the step of forming the model from wax.

3. A method according to claim 1 and further comprising disposing the selected one of the place holder and the second interconnecting element on the first interconnecting element (14) in the mouth of the dental patient, applying outside the mouth of the dental patient, on a respective region of the dental restoration on which the selected one of the place holder and the second interconnecting element is received, a curable material which can be hardened by light irradiation thereof, placing the dental restoration in the mouth of the dental patient, and hardening the curable material by light irradiation thereof to thereby create a secure interconnection between the selected one of the place holder and the second interconnecting element and the dental restoration.

4. A method according to claim 1, wherein at least a portion of the first interconnecting element (14) is formed of ceramic.

5. A method according to claim 1, wherein the first interconnecting element (14) and the selected one of the place holder and the second interconnecting element are configured as a positive coupling piece (22, 24) and a negative coupling piece (26, 28), respectively, which are securable to one another in a mated shape closure manner and the positive coupling piece (22, 24) and the negative coupling piece (26, 28) are formed of materials having substantially the same heat expansion coefficient.

6. A method according to claim 5, wherein the negative coupling piece (26, 28) is at least partially formed of glass fiber reinforced synthetic material.

* * * * *